United States Patent
Zhou et al.

(10) Patent No.: US 11,008,273 B2
(45) Date of Patent: May 18, 2021

(54) PROCESS FOR THE MANUFACTURE OF FLUORINATED BENZENES AND FLUORINATED BENZOPHENONES, AND DERIVATIVES THEREOF

(71) Applicant: Fujian Yongjing Technology Co., Ltd, Shaowu (CN)

(72) Inventors: Changyue Zhou, Shaowu (CN); Hongjun Du, Shaowu (CN); Wenting Wu, Shaowu (CN)

(*) Notice: Subject to any disclaimer, the term of this patent is extended or adjusted under 35 U.S.C. 154(b) by 0 days.

(21) Appl. No.: 16/792,174

(22) Filed: Feb. 14, 2020

(65) Prior Publication Data

US 2020/0262776 A1    Aug. 20, 2020

(30) Foreign Application Priority Data

Feb. 15, 2019    (DE) .................. 102019103838.3

(51) Int. Cl.
| | | |
|---|---|---|
| C07C 45/63 | (2006.01) | |
| B01J 27/12 | (2006.01) | |
| C07C 49/813 | (2006.01) | |

(52) U.S. Cl.
CPC ............... C07C 45/63 (2013.01); B01J 27/12 (2013.01); C07C 49/813 (2013.01)

(58) Field of Classification Search
CPC ........ C07C 45/63; C07C 49/813; B01J 27/12; C07F 9/90
See application file for complete search history.

(56) References Cited

U.S. PATENT DOCUMENTS

| | | | | |
|---|---|---|---|---|
| 2,731,416 A * | 1/1956 | Humphrey | ............... | C10M 1/08 508/457 |
| 2,734,927 A * | 2/1956 | Vollmann | ............... | C07C 17/361 570/190 |
| 2,805,264 A * | 9/1957 | Kissling | ................ | C07C 17/392 570/211 |
| 3,775,476 A * | 11/1973 | Rondestvedt | ........... | C07C 51/58 562/855 |
| 4,079,089 A * | 3/1978 | Klauke | ................. | C07C 17/206 570/145 |
| 4,207,266 A * | 6/1980 | Opie | ....................... | C07C 17/32 534/588 |
| 4,251,675 A * | 2/1981 | Engel | ...................... | C07C 2/861 585/422 |
| 4,453,009 A | 6/1984 | Yamaguchi et al. | | |
| 4,814,508 A | 3/1989 | Gors et al. | | |
| 5,061,810 A * | 10/1991 | Ramachandran | ....... | C07C 65/34 549/244 |
| 5,300,693 A | 4/1994 | Gilb et al. | | |
| 5,332,851 A * | 7/1994 | Kumai | ..................... | C07C 17/32 558/329 |
| 6,919,485 B2 * | 7/2005 | Grote | ..................... | A01N 35/04 504/348 |
| 7,576,088 B2 * | 8/2009 | Alanine | ................. | A61P 17/02 514/254.11 |
| 2001/0034465 A1 * | 10/2001 | Swain | ..................... | C07B 39/00 570/170 |
| 2002/0095052 A1 * | 7/2002 | Muller | .................. | C07C 255/50 562/492 |
| 2020/0262770 A1 * | 8/2020 | Du | ........................ | C07C 201/12 |
| 2020/0262775 A1 * | 8/2020 | Du | ........................ | C07C 201/12 |

FOREIGN PATENT DOCUMENTS

| | | | | |
|---|---|---|---|---|
| CN | 102295591 A | * | 12/2011 | |
| CN | 106008182 | | 10/2016 | |
| CN | 106045828 | | 10/2016 | |
| CN | 107573500 | | 1/2018 | |
| DE | 3531837 | | 3/1987 | |
| DE | 10326613 | | 12/2004 | |
| EP | 1637271 B1 | | 5/2011 | |
| GB | 1405851 A | * | 9/1975 | ............. C07C 45/63 |
| WO | WO2018055384 | | 3/2018 | |

OTHER PUBLICATIONS

P. Kovacic et al., 82 Journal of the American Chemical Society, 5740-5743 (1960) (Year: 1960).*
Y. Mo et al., 96 Journal of the American Chemical Society, 4659-4572 (1974) (Year: 1974).*
G. Yakobson et al., Synthesis, 345-364 (1980) (Year: 1980).*
L. Alig et al., 51 Journal of Medicinal Chemistry, 2115-2127 (2008) ("Alig") (Year: 2008).*
T. Mezhenkova et al., 207 Journal of Fluorine Chemistry, 59-66 (2018) (Year: 2018).*
English-Language Machine Translation CN-102295591-A (2011) (Year: 2011).*
F. Jensen et al., Journal of the American Chemical Society (Jun. 20, 1958) (Year: 1958).*
J. Sommer et al., 100 Journal of the American Chemical Society (1978) (Year: 1978).*

(Continued)

*Primary Examiner* — Alexander R Pagano

(57) ABSTRACT

The invention relates to a new process for the manufacture or synthesis, respectively, of fluorinated benzenes and fluorinated benzophenones, and derivatives thereof, in particular of fluorobenzenes and derivatives thereof. The present invention particularly pertains to a novel environmentally friendly process for the synthesis of fluorinated benzenes and benzophenones as raw materials for the manufacture of polyaryletherketones (PAEKs).

6 Claims, 3 Drawing Sheets

(56) References Cited

OTHER PUBLICATIONS

G.Olah et al., 94 Journal of the American Chemical Society (1972) (Year: 1972).*
G. Olah, 12 Angewandte Cheme, International Edition in English, 173-254 (1973) (Year: 1973).*
G.Olah et al., 96 Journal of the American Chemical Society (1974) (Year: 1974).*
R. Ramchandani, et al., 37 Tetrahedron Letters (1996) (Year: 1996).*
J. Serra et al., 137 Journal of the American Chemical Society, 13389-13397 (2015) (Year: 2015).*
M. Shekarchi et al., 147 Catalyst Letters (2017) (Year: 2017).*

* cited by examiner

PROCESS FOR THE MANUFACTURE OF FLUORINATED BENZENES AND FLUORINATED BENZOPHENONES, AND DERIVATIVES THEREOF

BACKGROUND OF THE INVENTION

Field of the Disclosure

The invention relates to a new process for the manufacture or synthesis, respectively, of fluorinated benzenes and fluorinated benzophenones, and derivatives thereof, in particular of fluorobenzenes and derivatives thereof.

Description of Related Art

Benzophenones are starting materials in the manufacture of Polyaryletherketone (PAEK).

Polyaryletherketone (PAEK) is a family of semi-crystalline thermoplastics with high-temperature stability and high mechanical strength whose molecular backbone contains alternately ketone ($R_L$-CO-$R_L$) and ether groups ($R_L$-O-$R_L$). The linking group $R_L$ between the functional groups consists of a 1,4-substituted aryl group, e.g. a 1,4-substituted benzene group. In the context of organic molecules, aryl is any functional group or substituent derived from an aromatic ring, usually an aromatic hydrocarbon, such as phenyl and naphthyl. The term "aryl" is used for the sake of abbreviation or generalization, and "Ar" is used as a placeholder for the aryl group in chemical structure diagrams.

Regarding properties of PAEK, PAEK has a continuous operating temperature of 250° C. (482° F.) and under short-term loads can function up to 350° C. (662° F.). When burned it has the least toxic and corrosive fumes. It also has a low heat output when burned, so it qualifies for use in interior aviation applications. It also has good overall chemical resistance. It has a tensile strength of 85 MPa (12,300 psi) and a Young's modulus of 4,100 MPa (590,000 psi). Its yield strength is 104 MPa (15,100 psi) at 23° C. (73° F.) and 37 MPa (5,400 psi) at 160° C. (320° F.).

PAEK plastics are characterized by phenylene rings that are linked via oxygen bridges (ether and carbonyl groups (ketone)). The ratio and sequence of ether to ketones mainly affects the glass transition temperature and melting point of the polymer. It also affects its heat resistance and processing temperature. The higher the ratio of ketones the more rigid the polymer chain, which results in a higher glass transition temperature and melting point. The processing temperatures can range from 350 to 430° C.

Plastics that fall within this family include PEK (polyetherketone), PEEK (polyetheretherketone), PEKK (polyetherketoneketone), PEEKK (polyetheretherketoneketone), PEKEKK (polyetherketoneetherketoneketone).

PAEKs can be produced in two ways, one is called the nucleophilic route and the other is called the electrophilic route. The nucleophilic route has the formation of ether linkages in the polymerization step. The electrophilic route has the formation of carbonyl bridges during the polymerization step. It can be processed using all of the typical thermoplastic processes, such as injection molding, extrusion, compression molding, and transfer molding.

PAEKs are suitable in the following applications. One major engineering application is oil drilling components, such as seals, compressor rings, valve parts, gears, bearings, and wire coatings. It is also used in the chemical pump industry because it can withstand the temperature, stress, and has the corrosion resistance. In the automotive industry it is used to make gears and thrust bearings in transmissions. Due to its excellent resistance to hydrolysis it is used in medical devices because it does not break down when sterilized. PEKEKK is used to make surgical implants, such as artificial hips.

Polyetheretherketone (PEEK) is a colourless organic thermoplastic polymer in the polyaryletherketone (PAEK) family, used in engineering applications. It was originally introduced by Victrex PLC, then Imperial Chemical Industries (ICI) in the early 1980s.

For example, the synthesis of PEEK can be as follows. PEEK polymers are obtained by step-growth polymerization by the dialkylation of bisphenolate salts. Typical is the reaction of 4,4'-difluorobenzophenone with the disodium salt of hydroquinone, which is generated in situ by deprotonation with sodium carbonate. The reaction is conducted around 300° C. in polar aprotic solvents—such as diphenyl sulphone.

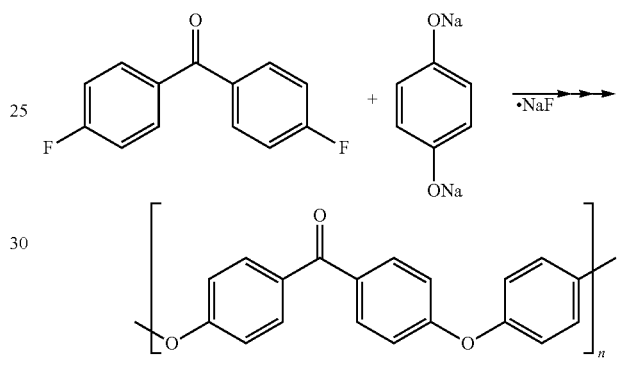

Regarding properties of PEEK, PEEK is a semicrystalline thermoplastic with excellent mechanical and chemical resistance properties that are retained to high temperatures. The processing conditions used to mold PEEK can influence the crystallinity and hence the mechanical properties. Its Young's modulus is 3.6 GPa and its tensile strength is 90 to 100 Mpa. PEEK has a glass transition temperature of around 143° C. (289° F.) and melts around 343° C. (662° F.). Some grades have a useful operating temperature of up to 250° C. (482° F.). The thermal conductivity increases nearly linearly with temperature between room temperature and solidus temperature. It is highly resistant to thermal degradation, as well as to attack by both organic and aqueous environments. It is attacked by halogens and strong Brønsted and Lewis acids, as well as some halogenated compounds and aliphatic hydrocarbons at high temperatures. It is soluble in concentrated sulfuric acid at room temperature, although dissolution can take a very long time unless the polymer is in a form with a high surface-area-to-volume ratio, such as a fine powder or thin film. It has high resistance to biodegradation.

PEEKs are suitable in the following applications. Because of its robustness, PEEK is used to fabricate items used in demanding applications, including bearings, piston parts, pumps, High-performance liquid chromatography columns, compressor plate valves, and electrical cable insulation. It is one of the few plastics compatible with ultra-high vacuum applications. PEEK is considered an advanced biomaterial used in medical implants (e.g. knee), and also use with a high-resolution magnetic resonance imaging (MRI), for creating a partial replacement skull in neurosurgical applications.

PEEK is finding increased use in spinal fusion devices and reinforcing rods. It is extensively used in the aerospace, automotive, and chemical process industries. PEEK seals and manifolds are commonly used in fluid applications. PEEK also performs well in applications where continuous high temperatures (up to 500° F./260° C.) are common. Because of this and its low thermal conductivity, it is also used in FFF printing to thermally separate the hot end from the cold end. Peek is also extensively used as an insulator inside of vaping atomizers, especially in rebuildable atomizers such as RDA's, RDTA's and RTA's. Its main function in vaping atomizers is separating the positive post from the negative post inside on the base of the atomizer.

Regarding benzophenone, the preferred IUPAC name is diphenylmethanone; other names include benzophenone, phenyl ketone, diphenyl ketone, benzoylbenzene, benzoylphenyl, benzoylphenyl, diphenylmethanone; the CAS Number is 119-61-9.

Benzophenone is the organic compound with the formula $(C_6H_5)_2CO$ generally abbreviated $Ph_2CO$. It is a white solid that is soluble in organic solvents. Benzophenone is a widely used building block in organic chemistry, being the parent diarylketone. Benzophenone can be used as a photo initiator in UV-curing applications such as inks, imaging, and clear coatings in the printing industry. Benzophenone prevents ultraviolet (UV) light from damaging scents and colors in products such as perfumes and soaps. Benzophenone can also be added to plastic packaging as a UV blocker to prevent photo-degradation of the packaging polymers or its contents. Its use allows manufacturers to package the product in clear glass or plastic (such as a PETE water bottle). Without it, opaque or dark packaging would be required. In biological applications, benzophenones have been used extensively as photophysical probes to identify and map peptide-protein interactions. Benzophenone is used as an additive in flavorings or perfumes for "sweet-woody-geranium-like notes.

In the prior art benzophenone is produced by the copper-catalyzed oxidation of diphenylmethane with air. A laboratory route involves the reaction of benzene with carbon tetrachloride followed by hydrolysis of the resulting diphenyldichloromethane. It can also be prepared by Friedel-Crafts acylation of benzene with benzoyl chloride in the presence of a Lewis acid (e.g., aluminum chloride) catalyst. Another route of synthesis is through a palladium(II)/oxometalate catalyst. This converts an alcohol to a ketone with two groups on each side. Another, less well-known reaction to produce benzophenone is the pyrolysis of anhydrous calcium benzoate.

Regarding properties, diphenyldichloromethane is an organic compound with the formula $(C_6H_5)_2CCl_2$. It is a colorless solid that is used as a precursor to other organic compounds.

Diphenyldichloromethane is prepared from carbon tetrachloride and anhydrous aluminum chloride as catalyst in a double Friedel-Crafts alkylation of benzene. Alternatively, benzophenone is treated with phosphorus pentachloride:

$(C_6H_5)_2CO+PCl_5\rightarrow(C_6H_5)_2CCl_2+POCl_3$

Diphenyldichloromethane undergoes hydrolysis to benzophenone:

$(C_6H_5)_2CCl_2+H_2O\rightarrow(C_6H_5)_2CO+2HCl$

Diphenyldichloromethane is used in the synthesis of tetraphenylethylene, diphenylmethane imine hydrochloride and benzoic anhydride.

Regarding diphenylmethane, diphenylmethane is an organic compound with the formula $(C_6H_5)_2CH_2$. The compound consists of methane wherein two hydrogen atoms are replaced by two phenyl groups. Diphenylmethane forms a common skeleton in organic chemistry; the diphenylmethyl group is also known asbenzhydryl. It is prepared by the Friedel-Crafts alkylation of benzyl chloride with benzene in the presence of a Lewis acid such as aluminum trichloride:

$C_6H_5CH_2Cl+C_6H_6\rightarrow(C_6H_5)_2CH_2+HCl$

The so-called Friedel-Crafts reactions are well known to the persons skilled in the art. For example, Friedel-Crafts reactions are known as a set of reactions developed by Charles Friedel and James Crafts in 1877 to attach substituents to an aromatic ring. Friedel-Crafts reactions are of two main types: alkylation reactions and acylation reactions. Both proceed by electrophilic aromatic substitution.

PAEKs like Polyetheretherketone (PEEK) are used in specialty plastics applications like described in WO2018/055384 by Victrex.

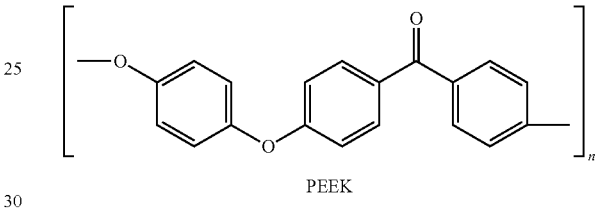

PEEK

PEEK is made out of condensation of Hydroquinone with 4,4'-difluorobenzophenone, and this benzophenone is made out of fluorobenzene as key raw material like described in Victrex WO2018/055384 and also patents in Faming ZhuanliShenqing (2018), CN 107573500. The 4,4'-difluorobenzophenone is either made out of 4,4'-difluorodiphenylmethane by oxidation (ChemCatChem (2018), 10(5), 1096-1106) or alternatively out of Friedel-Crafts alkylation reaction of fluorobenzene with $CCl_4$ (HuagongJinzhan (2015), 34(4), 1104-1108) or Friedel-Crafts acylation of fluorobenzene with 4-fluorobenzoylchloride like mentioned in Raychem's U.S. Pat. No. 4,814,508. The most common synthesis of difluorodiphenylmethane as of today is the synthesis out of 4,4'-methylenebis[benzenamine] by Balz-Schiemann reaction involving dirty $NaNO_2/HBF_4$ chemistry like described by Faming ZhuanliShenqing (2016), in CN 106008182, and by other authors. The synthesis of difluorodiphenylmethane out of fluorobenzene and formaldehyde is described in early days already in Bulletin de la SocieteChimique de France; (1951); p. 318,323 or out of 4-fluorobenzylchloride like in Journal of the Chemical Society, Chemical Communications (1989)(18), 1353-4.

Another Friedel-Crafts acylation based synthesis of 4,4'-difluorobenzophenone is out of fluorobenzene, or alternatively starting from 4-fluorophenylboronic acid like described in Chemical Communications (Cambridge, United Kingdom) (2017), 53(93), 12584-12587 and a 4-fluorobenzoic acid derivative or 4-fluorotrichlorotoluene derivative like described in Faming ZhuanliShenqing (2016), CN 106045828. All these processes involve at least in one of the steps a Balz-Schiemann reaction combined with a Friedel-Crafts reaction. Both reaction types are quite old technologies which might have to be replaced by newer environmentally friendly chemistries and reaction technologies. The synthesis of 4,4'-difluorobenzophenone out of 4,4'-dichlorobenzophenone by "dirty" Halex reaction is described in Mitsui's U.S. Pat. No. 4,453,009. The said Halex chemistry in general is considered "dirty" due to incomplete conversion, and isolation of product is challenging and often produces large amounts toxic waste water. The "dirty" KCl obtained as coupling product is often used for landfill.

In general a Friedel-Crafts reaction of benzoylchloride with chlorobenzene in state of the art reactors (Lewis acid catalyzed in ionic liquids) is known as described in Chemistry Letters (2008), 37(8), 844-845 and Journal of the Chinese Chemical Society (Taipei) (2000), 47(6), 1243-1246, also the Friedel-Craft in microreactors with $\alpha$-$Fe_2O_3$ and $CaCO_3$ nanoparticles is already described like in Chemical Engineering Journal (Amsterdam, Netherlands) (2018) 331, 443-449. The Friedel-Crafts reaction of chlorobenzene with chlorobenzoylchloride with $AlCl_3$ as Lewis acid is described with 96% yield in HuagongXinxingCailiao (2012), 40(2), and 87-90% and in Journal of Fluorine Chemistry (2005), 126(8), 1191-1195 by using rare earth (III) perfluorooctane sulfonates in fluorous solvents with 86% yield.

The reaction of chlorobenzene with terephtaloylchloride is known from KhimicheskayaTekhnologiya (Moscow, Russian Federation) (2001)(5), 3-5, at temperatures around 260° C. without Friedel-Crafts Catalyst and with 86% yield and also in Qingdao KejiDaxueXuebao, ZiranKexueban (2007), 28(1), 39-42 using $AlCl_3$ and Jpn. KokaiTokkyoKoho (2014), JP 2014237738 using $FeCl_3$ as Lewis acid.

Friedel-Crafts reaction of chlorobenzylchloride and chlorobenzene is described in Journal of Organic Chemistry (1989), 54(5), 1201-3, and AngewandteChemie, International Edition (2011), 50(46), 10913-10916.

All known above reactions either produce lots of waste and waste water, require expensive reagents or are not practicable in industrial scale especially in respect to environment. Object of the present invention is to overcome the disadvantages of the prior art processes, in particular to provide a more efficient and energy saving processes, also more environmentally friendly process, for the manufacture of compounds by Friedel-Crafts reaction, and to provide a beneficially catalyst therefore. Another object of the invention is to employ a Friedel-Crafts reaction, and to employ a beneficially catalyst therefore, which can easily be combined with a fluorination reaction, wherein the fluorination reaction may be prior to the Friedel-Crafts reaction, or may be after the Friedel-Crafts reaction. Herein it is still another object of the invention to employ a catalyst for the Friedel-Crafts reaction which catalyst may be used in both, the Friedel-Crafts reaction and the fluorination reaction.

SUMMARY OF THE INVENTION

The objects of the invention are solved as defined in the claims, and described herein after in detail. Accordingly, the invention relates to a new process for the manufacture of fluoroaryl compounds and derivatives thereof, in particular of fluorobenzenes and derivatives thereof, and especially wherein said manufacture, as defined in the claims and as further described herein, relates to an environmentally friendly production of the said compounds.

Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for the manufacture of nuclear fluorinated aromatics, and preferably of nuclear fluorinated fluorobenzenes.

In particular, in one aspect, the present invention pertains to a novel environmentally friendly process for the synthesis of fluorinated benzenes and benzophenones as raw materials for the manufacture of polyaryletherketones (PAEKs). Herein, the invention involves the manufacture or synthesis, respectively, of acylated or alkylated aryl compounds, for example, acylated or alkylated benzenes, by the so-called Friedel-Crafts reaction, and a new catalyst therefore.

In the context of organic molecules, aryl is any functional group or substituent derived from an aromatic ring, usually an aromatic hydrocarbon, such as phenyl and naphthyl. The term "aryl" is used for the sake of abbreviation or generalization, and "Ar" is used as a placeholder for the aryl group in chemical structure diagrams.

A simple aryl group is phenyl (with the chemical formula $C_6H_5$), a group derived from benzene. The most basic aryl group is phenyl, which is made up of a benzene ring with one hydrogen atom substituted for some substituent, and has the molecular formula $C_6H_5$—. To name compounds containing phenyl groups, the phenyl group can be taken to be the parent hydrocarbon and being represented by the suffix "-benzene". Alternatively, the phenyl group could be treated as the substituent, being described within the name as "phenyl". This is usually done when the group attached to the phenyl group consists of six or more carbon atoms.

The Friedel-Crafts alkylation involves the alkylation of an aromatic ring with an alkyl halide using a strong Lewis acid catalyst. With anhydrous ferric chloride as a catalyst, the alkyl group attaches at the former site of the chloride ion. This reaction suffers from the disadvantage that the product is more nucleophilic than the reactant. Consequently, overalkylation occurs. Furthermore, the reaction is only very useful for tertiary alkylating agents, some secondary alkylating agents, or ones that yield stabilized carbocations (e.g., benzylic ones). In the case of primary alkyl halides, the incipient carbocation ($R^{(+)}$—X—$Al^{(-)}$—$Cl_3$) will undergo a carbocation rearrangement reaction.

The Friedel-Crafts acylation involves the acylation of aromatic rings. Typical acylating agents are acyl chlorides. Typical Lewis acid catalysts are acids and aluminum trichloride. Friedel-Crafts acylation is also possible with acid anhydrides. Reaction conditions are similar to the Friedel-Crafts alkylation. This reaction has several advantages over the alkylation reaction. Due to the electron-withdrawing effect of the carbonyl group, the ketone product is always less reactive than the original molecule, so multiple acylations do not occur. Also, there are no carbocation rearrangements, as the acylium ion is stabilized by a resonance structure in which the positive charge is on the oxygen. The viability of the Friedel-Crafts acylation depends on the stability of the acyl chloride reagent.

A compound of relevance in the context of the present invention is terephthaloyl chloride (TCL, 1,4-benzenedicarbonyl chloride), also known as terephthalic acid dichloride. The preferred IUPAC name is benzene-1,4-dicarbonyl dichloride. Other names are terephthaloyl dichloride, 1,4-benzenedicarbonyl chloride, benzene-1,4-dicarbonyl chloride, terephthalic acid dichloride, terephthaloyl dichloride, p-phthalyl chloride; and a common abbreviation is TCL.

As stated before, all reactions known in the prior art either produce lots of waste and waste water, require expensive reagents or are not practicable in industrial scale.

The disadvantages of the prior art are overcome by the present invention. Hence, this present invention provides a process without waste water, reasonable prices reagents and suitable for industrial scale. More particularly the object is solved by using very cheap clean and easy to make starting materials, and by using SbHal$_5$ based catalyst systems. The invention is also very advantageous even if fluorinated compounds are intended to be prepared, and furthermore, in one embodiment the Friedel-Crafts reaction of the invention optionally is performed in microreactor systems.

Accordingly, in one aspect of the invention, an industrially beneficial process for preparing fluorobenzenes from halobenzene precursors using HF to form hydrogen halide is provided by the present invention. In addition, the invention provides for a beneficial and surprisingly simple use of chlorobenzene as an industrially interesting starting material in the manufacture of fluorobenzene, which use of chlorobenzene was not known in the prior art before the present invention.

The Catalyst:

The processes of the invention employ a halogenation catalyst, preferably a fluorination catalyst which also can be—but not exclusively—a so called Lewis acid. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially as Sb fluorination catalysts providing the active species $H_2F^+SbF_6^-$, if SbHal$_5$ is kept in an excess of HF for a fluorination step prior or subsequent to the Friedel-Crafts reaction, but wherein in the Friedel-Crafts reaction itself the HF is used in "low" concentration only, e.g. in the ppm-range.

Thus, if a fluorination catalyst normally used with excess of HF in an industrially beneficial process for preparing fluorobenzenes from halobenzene precursors using HF to form hydrogen halide, in addition the fluorination catalyst can also provide for a beneficial and simple use as a Friedel-Crafts catalyst if HF is used in "low" concentration, or HF is absent, and thus provides new opportunities of providing acylated or alkylated compounds as industrially interesting starting materials for the manufacture of compounds by Friedel-Crafts reaction, in a manner that was not known in the prior art before the present invention. The term "low" concentration is defined more particularly herein below in the detailed description of the invention.

According to the invention, antimony (Sb) is the best and cheapest catalyst, but As and Bi are also possible to be used as fluorination catalyst, and if desired also for the Friedel-Crafts reaction, in the oxidation stage III of the metals, especially in the presence of SbHal$_5$ with a SbHal-III share, or with share of other metal compounds like MHal$_3$ compounds, e.g., AsHal$_3$ and BiHal$_3$.

For example, in one aspect of the invention, the application of antimony (Sb) catalysts for the manufacture of nuclear fluorinated aromatic systems ("fluorobenzenes") is new and advantageous. The catalyst, for example, is SbF$_5$ in HF, made naturally from SbCl$_5$. At the beginning of the reaction with fresh catalyst, of course, one or two chlorine atoms on the antimony (Sb) of the catalyst can be exchanged, and all Chlorine atoms will be exchanged after a certain time of performing the fluorination.

So far, for example, fluorobenzene and derivatives are industrially made with BalzSchiemann or Sandmeyer reaction. These two types of reactions are chemically very good but disadvantageously cause a lot of waste, and also in the form of very toxic wastewater. For this reason, even entire chemical plants are currently closed, e.g., in China, and many companies worldwide are now without reliable and environmentally acceptable fluorobenzene sources. Same or similar problems described here by example of fluorobenzene may generally be also applicable to the preparation of other fluorinated aromatic and heteroaromatic compounds, e.g., such as used as building blocks in the pharmaceutical and agrochemical field.

The chemical novelty and concept of the invention is that a new fluorination process with use of halogenation catalysts, e.g., in preferred embodiments antimony (Sb) halides as halogenation catalysts, as used in the invention and described herein, now are provided in manufacturing processes to catalytically produce fluorobenzene and derivatives thereof, in particular without any (at least not any significant) waste by-products. The process of the invention, for example, only produces marketable hydrogen chloride (HCl) grades after some purification e.g. some quite simple distillation under pressure. For example, at 15 bar and −20° C. temperature at the column head, there is 100% HCl at the column head.

The Reactors:

In addition to the above, according to one aspect of the invention, also a plant engineering invention is provided, as used in the process invention and described herein, pertaining to the optional, and in some embodiments of the process invention, the process even preferred implementation in microreactors.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let formed HCl to escape and to positively influence the reaction performance. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

DESCRIPTION OF THE INVENTION

Figure 1:
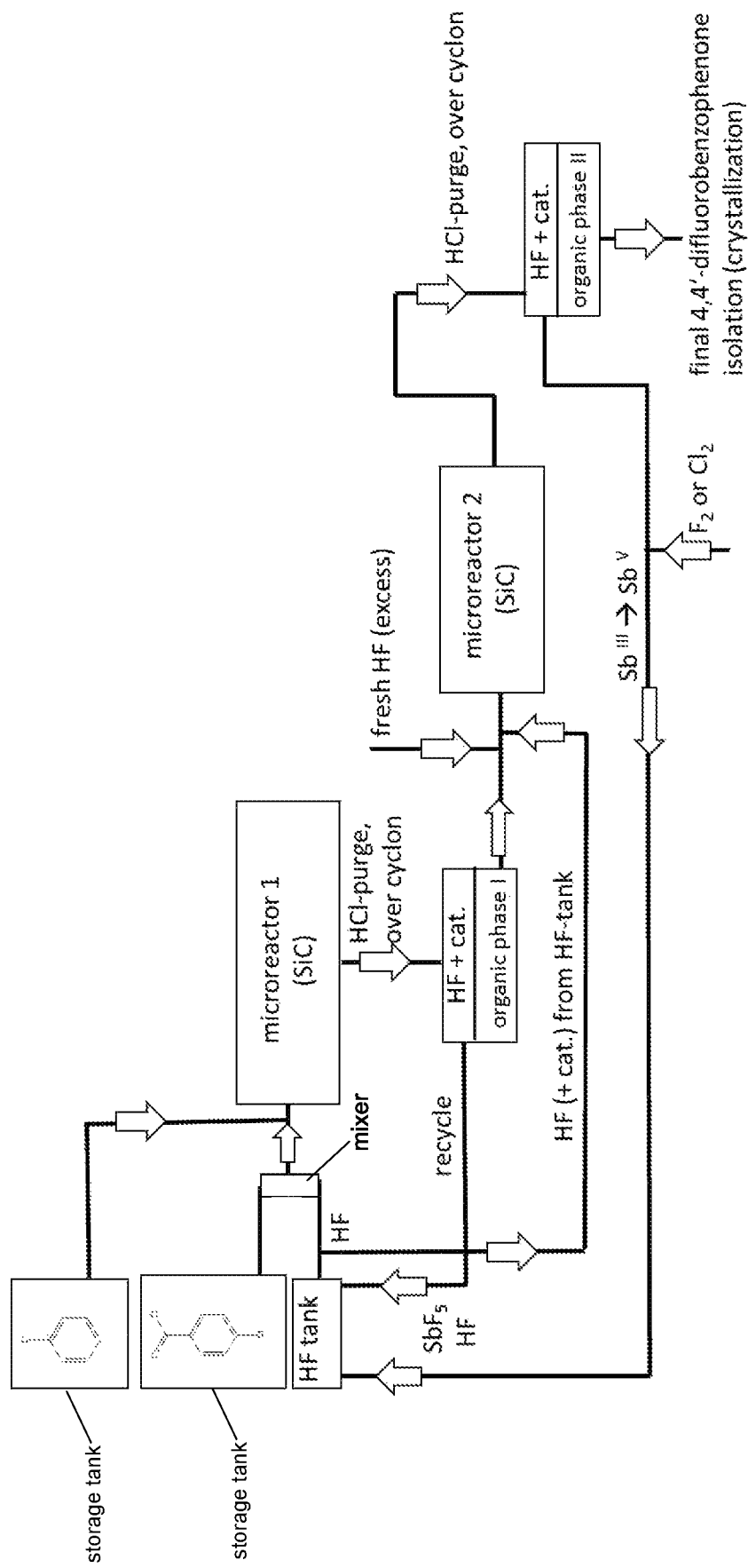
In FIG. 1, shows an exemplary embodiment of a process scheme for the continuous manufacture of 4,4'-difluorobenzophenone out of 4-chlorbenzoylchloride and chlorobenzene, for example, by synthesis in microreactor.

As briefly described in the Summary of the Invention, and defined in the claims and further detailed by the following description and examples herein, the invention overcomes the shortage of the state of the art that, prior to this invention, there is no industrially suitable process for preparing fluorobenzenes from halobenzene precursors using HF to form hydrogen halide.

Thus, as already mentioned, in one aspect of the invention, an industrially beneficial process for preparing fluorobenzenes from halobenzene precursors using HF to form hydrogen halide is provided by the present invention. In addition, the invention provides for a beneficial and surprisingly simple use of chlorobenzene as an industrially interesting starting material in the manufacture of fluorobenzene, which use of chlorobenzene was not known in the prior art before the present invention.

As explained supra, there is no industrially suitable process for preparing fluorobenzenes from halobenzene precursors using HF to form hydrogen halide. Since hydrogen fluoride is the first chemically utilizable stage according to the natural resource fluorspar ($CaF_2$), which is obtained from mines, and the hydrogen halide according to the invention can be further used in chemical syntheses, the catalyzed halogen-fluorine exchange on aromatics is the best environmental and process technology imaginable procedures. This is achieved by the present invention.

Antimony pentafluoride in an excess of anhydrous HF gives the superacid $H_2F^+$ $SbF_6^-$, a strongly nucleophilic fluoride atom. It has just been found that highly fluorinated $SbF_5$ in anhydrous HF as a solvent fluorinates benzenes and even deactivated halogenobenzenes in a nucleophilic exchange reaction, especially chlorobenzene, and bromobenzene and derivatives, also very deactivated precursors can be used as starting materials. This is represented by the general scheme:

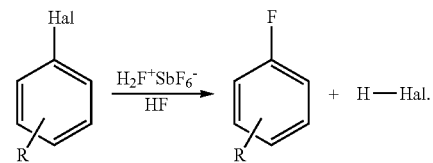

Sb-pentahalides, as such in inert solvents such as perfluorinated solvents, would function mainly as a Lewis acid and, upon hydrolysis, would provide phenols and biphenyls. Only if $SbHal_5$ undergoes a reduction to $SbHal_3$ a halogenation is possible, but not catalytically. Reactions of antimony pentafluorides with chlorobenzenes are unknown, and the skilled person would normally expect Friedel-Crafts products or just a polymerisation, decomposition or formation of undefined products and oligomers. In Journal of the Chemical Society, Perkin Transactions 2: Physical Organic Chemistry (1997) (11), 2301-2306 a reaction of chlorobenzene with phenyl disulfide is described, here $SbCl_5$ acts as a Friedel-Crafts catalyst, not as a halogenating reagent. In Theoretical and Experimental Chemistry (2011), 47 (2), 123-128, $SbCl_5$ is part of a chlorinating reagent for the scientific production of dichlorobenzene together with crown ethers and chlorine gas, but this may not be suitable as an industrial process.

However, according to the present inventions findings, if the reaction is carried out in anhydrous HF as solvent and in a temperature range starting at slightly higher temperature than ambient temperature, the nucleophilic halogen-fluorine exchange takes place in very good yields and rapid reaction rates because in (excess) HF, surprisingly, a change of functionality of the antimony pentahalide from a Friedel-Crafts catalyst function to the nucleophilic fluorination functionality, or to the fluorination agent, according to the present invention takes place, and namely in the form the super-acidic very strongly nucleophilic fluorine anion ($F^-$) which is offered to, e.g., the chlorobenzene as a reaction partner, and preferably to produce a nuclear fluorinated fluorobenzene. For example, in case of more active, the fluorination can take place already at a temperature starting from of about 40° C. But slightly higher temperatures than the said 40° C., of course, are also advantageous for bringing HCl, once formed, into the gas phase, and thereby the fluorination reaction is accelerated. Since antimony (Sb) in oxidation stage V (i.e., Sb-V) decomposes (at least partially) to Sb-III at a temperature starting from about 130° C., and even without any reactants being present, the upper reaction temperature should not be too high. Accordingly, in one embodiment, the temperature of the fluorination reaction is in the range of from about 40° C. to 130° C. In a preferred embodiment, the temperature of the fluorination reaction is in the range of from about 40° C. to 110° C., more preferably in the range of from about 50° C. to 110° C., even more preferably in the range of from about 60° C. to 110° C., and still more preferably in the range of from about 70° C. to 110° C. Most preferably, the temperature of the fluorination reaction is in the range of from about 80° C. to 110° C., which is the optimal temperature range. The preceding applies to all chlorobenzenes and chlorobenzene derivatives, including chlorobenzenes with chemically deactivating substituents such as other halogens or strong-pulling substituents such as cyano or nitro groups. Similarly, this applies to the manufacture other nuclear fluorinated aromatics, if such other nuclear fluorinated aromatics shall be produced from the corresponding nuclear chlorinated aromatics as the starting material. For example, but without wishing to be bound to a theory, in nucleophilic reactions, substituents such as CN and $NO_2$, which otherwise normally are deactivating, herein increase the reactivity towards nucleophiles, because electrons are attracted to the substituent, and thus the delta+ is increased at other positions and in the aromatic ring.

The disadvantages of the prior art are overcome by the present invention. Hence, this present invention provides a process without waste water, reasonable prices reagents and suitable for industrial scale. More particularly object is solved by using very cheap clean and easy to make starting materials, and by using $SbHal_5$ based catalyst systems. The invention is also very advantageous if fluorinated compounds are intended to be prepared.

A process without waste water, reasonable prices reagents and suitable for industrial scale is provided by the present invention. More particularly the object is solved by using chlorobenzene and/or chlorobenzene derivatives as very cheap clean and easy to make starting materials and $SbHal_5$ based catalyst systems in one embodiment optionally performed in microreactor systems; chemistry is given in the following schemes for some options, as examples, but without thereby intending to limit the invention.

Compounds shown in brackets [structure] may be formed in situ.

Scheme1: CCl4-option (one pot) batch or continuous (inventive procedure).

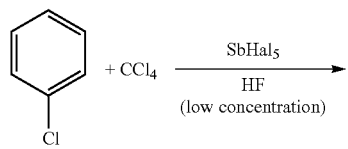

It is supposed that the two chlorine atoms at the methylene bridge may be also fluorinated, at least in part, because the corresponding intermediates (benzyl cation, before the $F^-$is introduced) are very well stabilized by the benzyl structures. Therefore, the preliminary stage before the hydrolysis stage can also be the corresponding difluoromethylene compound and/or the mixed fluoro-chloro-methylene compound.

Scheme 2: 4-Chlorobenzoic acid chloride option, (one pot) batch or continuous (inventive procedure).

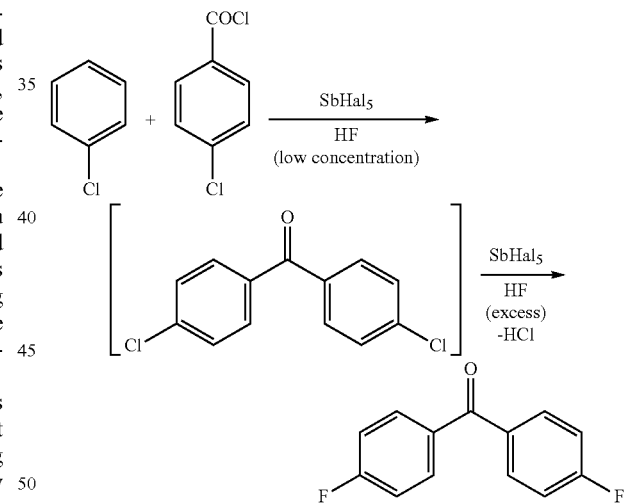

Alternatively to the use of 4-chlorobenzoic acid chloride, according to the invention it is also possible to use of p-chlorophenylboronic acid as another option. The reaction could be done in batch in one or several batch reactors or continuously in microreactor systems. The organic material is preferred separated from catalyst and HF by phase separation. To speed up the phase formation, or depending on the compounds, an inert solvent can be added. Certainly, there are cases (e.g., in case of fluorobenzene derivatives), in which an inert solvent in the first phase allows the phase separation at all. Therefore, the invention generally also includes a process wherein the phase separation is performed in the presence of an added inert solvent. Herein, the meaning of "inert solvent" is that the solvent is inert under the reaction conditions, and in particular does not undergo fluorination under the reaction conditions. The isolated organic material is subjected to further purification by crystallization (MP: 107° C.).

Scheme 3: Difluorodiphenylmethane can be prepared out of chlorobenzene and 4-chloro-1-(chloromethyl)benzene followed by fluorination in SbHal$_5$/HF-system (inventive procedure).

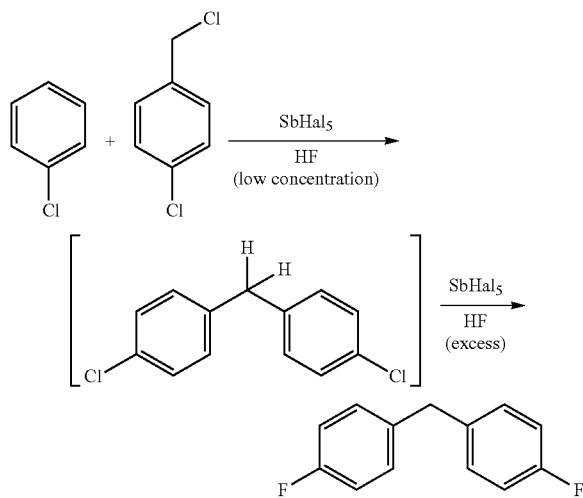

Another interesting molecule as raw material for PAEKs is one in which the synthesis is done again with classical Friedel-Crafts out of terephthaloylchloride and fluorobenzene like described in XiangsuZiyuanLiyong (2011)(2), 1-4, or Hoechst No U.S. Pat. No. 5,300,693 and BASF patent No DE3531837.

Scheme 4: Conversion of terephtaloylchlodie with chlorobenzene followed by fluorination in SbHal$_5$/HF-system (inventive procedure).

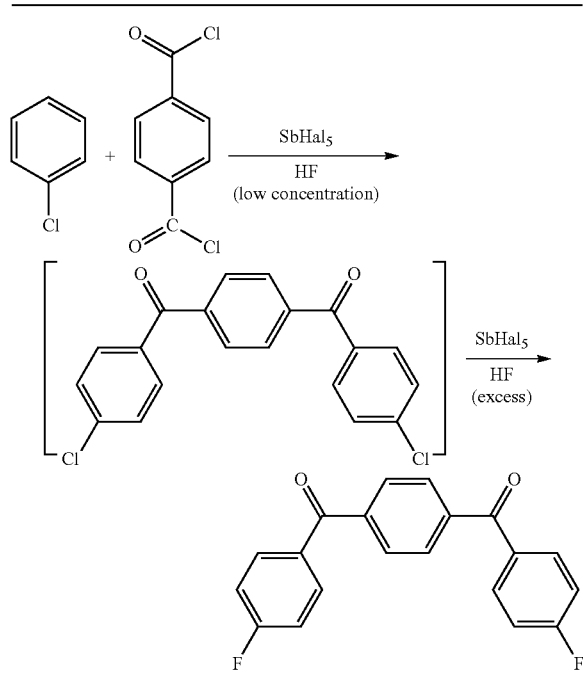

If alternatively fluorobenzene is used instead of chlorobenzene, just the Friedel-Crafts step is applied, and is as claimed in present invention.

All the inventive reactions can be performed in batch reactors (autoclaves) either lined with HDPTFE or SiC-equipment or continuously in microreactors or plug flow reactors. A series of STRs ("stirred vessels") is also possible, but plug flow and microreactor are more advantageous. It is to be noted that aluminum and aluminum alloys also exhibit some resistance, e.g., after fluorination of the surface, against highly fluorinated Sb-catalyst, and therefore, aluminum and aluminum alloys may also be employed as reactor material. The use of materials containing aluminum oxide or nickel and aluminum for producing or coating corrosion-resistant machine shafts in contact with chemically aggressive media is, for example, described in DE10326613. However, as SiC and HDPTFE normally are superior in resistance, they are preferred materials.

Of course, the Friedel-Crafts reaction of 4-chlorobenzoylchloride, 4-chlorobenzylchloride and terephtaloylchloride could be performed by known methods, other than the inventive method disclosed herein, but when using the inventive process described herein, additional separation steps are avoided, the product yield is increased and formation of waste is sharply reduced.

Scheme 5: Acylation of chlorobenzene according to the invention.

Scheme 6: Acylation of fluorobenzene according to the invention.

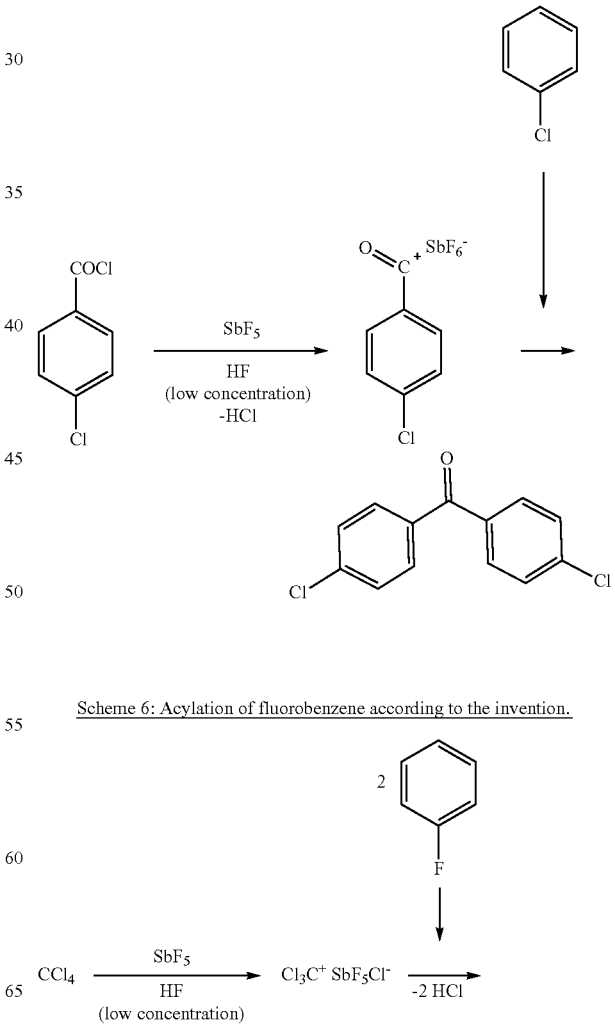

-continued

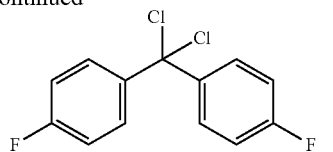

Here again, the difluoromethylene compound or at least the chloro-fluoro-methylene compound could arise, analogously, as noted in the context of scheme 1 above.

Scheme 7: Preparation of 4,4'-difluorophenylmethane by acylation of chlorobenzene according to the invention.

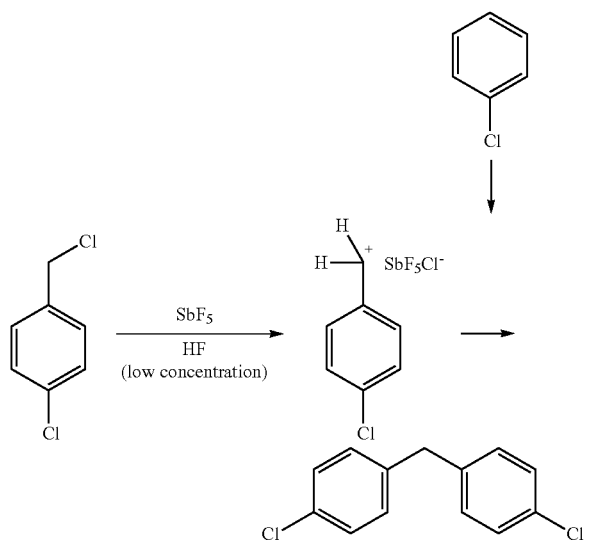

In the following, the general embodiments of the invention shall be described in more detail, to illustrate breadth of the invention that is duly explored and based a skilled person's educated guess, and thus derivable from the more specific embodiments described further below.

In a first embodiment, the invention pertains to a process of preparing a compound, in particular a compound comprising one or more aromatic rings, by Friedel-Crafts reaction, characterized in that an aromatic ring of a starting material compound that serves as a precursor of a PAEK, is reacted with a Friedel-Crafts reagent in the presence of an antimony pentahalide catalyst (SbHal$_5$), preferably in the presence of an activated antimony pentahalide catalyst (SbHal$_5$), optionally activated by hydrogen fluoride (HF).

The term "PAEK" is described herein supra, and accordingly is defined as known to the person skilled in the art, as well as the compounds that serve as a precursor of "PAEK". Reference is made to the said section and description above, which is incorporated herein in the context of the invention.

In a second embodiment, the invention pertains to a process of preparing a compound according as defined herein before, wherein the compound prepared is a fluorinated compound.

In a third embodiment, the invention pertains to process of preparing a compound according to the invention, wherein a starting material compound is selected from compounds having the formula (I):

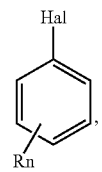

wherein, in principle, the residue Rn can be any substituent that is "inert" under the reaction conditions of fluorination and Friedel-Crafts reaction; including, e.g., ring systems, and including inert heterocycles are possible to be used in the invention, but preferably wherein Rn independently denotes one or more substituents selected from the group consisting of hydrogen (H), fluorine (F) or chlorine (Cl); and Hal denotes a halogen selected from fluorine (F), chlorine (Cl), bromine (Br) or Iodine (I); preferably fluorine (F) or chlorine (Cl).

In a forth embodiment, the invention pertains to a process of preparing a compound according to the invention, wherein the starting material compound is selected from compounds having the formula (I) as defined herein above, wherein Rn independently denotes a single substituent selected from the group consisting of hydrogen (H), fluorine (F), or chlorine (Cl); and Hal denotes a halogen selected from fluorine (F) or chlorine (Cl), preferably chlorine (Cl).

For example, in the process of preparing a compound as defined above, according to the invention, the starting material compound is selected from the group of compounds consisting of compounds wherein one of Rn, preferably a Rn in para-position (4-Rn), is fluorine (F) or chlorine (Cl), and the others of Rn are hydrogen, and Hal is fluorine (F) or chlorine (Cl); preferably wherein the starting material compound is selected from the group of compounds consisting of the compounds chlorobenzene, dichlorobenzene, preferably 1,4-dichlorobenzene, fluorobenzene, and difluorobenzene, preferably 1,4-difluorobenzene, more preferably wherein the starting material compound is selected from the group of compounds consisting of the compounds chlorobenzene and fluorobenzene.

In a fifth embodiment, the invention pertains to a process of preparing a compound according to any one of the embodiments of the invention above, wherein a Friedel-Crafts reagent is selected from compounds having the formula (II):

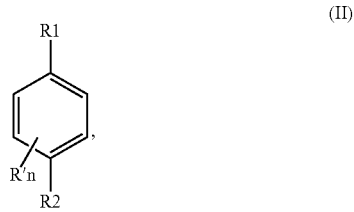

wherein
R'n independently denotes one or more substituents selected from the group consisting of hydrogen (H), fluorine (F) or chlorine (Cl; and;
R1 and R2 independently from each other denote a hydrogen, a tri-halogeno methyl group (—CHal$_3$), a halogeno carbonyl group (—(C=O)Hal) or a halogeno methyl group (—CH$_2$Hal), and at least one of R1 and R2 is a tri-halogeno methyl group (—CHal$_3$), a halogeno carbonyl group (—(C=O)Hal) or a halogeno methyl group (—CH$_2$Hal), and wherein each halogen (Hal) is selected from fluorine (F), chlorine (Cl), bromine (Br) or Iodine (I), preferably wherein the halogen (Hal) is selected from fluorine (F) and chlorine (Cl), more preferably wherein the halogen (Hal) is chlorine (Cl); and a boronic acid group.

A boronic acid is a compound related to boric acid (B(OH)$_3$) in which one of the three hydroxyl groups is replaced by an alkyl or aryl group. The general structure of a boronic acid is R"—B(OH)$_2$, wherein R" is a substituent. As a compound containing a carbon-boron bond, members of this class thus belong to the larger class of organoboranes. Boronic acids act as Lewis acids.

In principle, the residue R'n can be any substituent that is "inert" under the reaction conditions of fluorination and Friedel-Crafts reaction; including, e.g., ring systems, and including inert heterocycles are possible to be used in the invention.

For example, in the process of preparing a compound as defined above, according to the invention, a Friedel-Crafts reagent is selected from compounds having the formula (II) as defined above,
wherein
R'n independently denotes a single substituent selected from the group consisting of hydrogen (H), fluorine (F), or chlorine (Cl); and
R1 and R2 independently from each other denote a hydrogen, a trichloromethyl group (—CCl$_3$), a carbonyl chloride group (—(C=O)Cl) or a chloromethyl group (—CH$_2$C$_1$), and at least one of R1 and R2 is a trichloromethyl group (—CCl$_3$), a carbonyl chloride group (—(C=O)Cl) or a chloromethyl group (—CH$_2$C$_1$), or a boronic acid group.

For example, in the process of preparing a compound as defined above, according to the invention, the Friedel-Crafts reagent is selected from compounds having the formula (II) as defined in above, wherein R1 and R2 independently from each other denote a hydrogen, a carbonyl chloride group (—(C=O)Cl) or a chloromethyl group (—CH$_2$C$_1$), or a boronic acid group, and at least one of R1 and R2 is a carbonyl chloride group (—(C=O)Cl) or a chloromethyl group (—CH$_2$C$_1$) or a boronic acid group.

For example, in the process of preparing a compound as defined above, according to the invention, the Friedel-Crafts reagent is selected from the group compounds consisting of chlorobenzoic acid chloride, fluorobenzoic acid chloride, (4-chlorophenyl) boronic acid, benzenedicarbonyl dichloride and chloromethyl chlorobenzene, preferably 4-chlorobenzoic acid chloride, benzene-1,4-dicarbonyl dichloride, and 4-(chloromethyl)-1-chlorobenzene.

For example, in the process of preparing a compound as defined above, according to the invention, the Friedel-Crafts reagent is selected from compounds having the formula (II) as defined above, wherein a tri-halogeno methyl group (—CHal$_3$), or a trichloromethyl group (—CCl$_3$), respectively, is prepared in situ from tetrahalogenomethane in the process as defined above, or is prepared in situ from tetrachloromethane in the process as defined above, in the presence of the starting material compound.

For example, in the process of preparing a compound as defined above, according to the invention, the Friedel-Crafts reagent is prepared in situ from tetrahalogenomethane, and the starting material compound is chlorobenzene and fluorobenzene.

In another embodiment, the invention pertains to a process of preparing a compound according to the invention as defined above, wherein an aromatic ring of a starting material compound is reacted with a Friedel-Crafts reagent in the presence of an antimony pentahalide catalyst (SbHal$_5$), preferably in the presence of an antimony pentahalide catalyst (SbHal$_5$) activated by hydrogen fluoride (HF), characterized in that (i) 2 mole of chlorobenzene as a starting material compound is reacted with 1 mole of tetrachloromethane as a Friedel-Crafts reagent to produce as targeted compound (4,4'-dichlorodiphenyl)-dichloromethane;

(ii) 2 mole fluorobenzene as a starting material compound is reacted with 1 mole of tetrachloromethane as a Friedel-Crafts reagent to produce as targeted compound (4,4'-dichlorodiphenyl)-dichloromethane;

(iii) 1 mole of chlorobenzene as a starting material compound is reacted with 1 mole of 4-chlorobenzoic acid chloride as a Friedel-Crafts reagent to produce as targeted compound (4,4'-dichloro)-benzophenone;

(iv) 1 mole of chlorobenzene as a starting material compound is reacted with 1 mole of (4-chlorophenyl) boronic acid as a Friedel-Crafts reagent to produce as targeted compound (4,4'-dichloro)-benzophenone;

(v) 1 mole of fluorobenzene as a starting material compound is reacted with 1 mole of 4-chlorobenzoic acid chloride as a Friedel-Crafts reagent to produce as targeted compound (4-fluoro,4'-chloro)-benzophenone;

(vi) 1 mole of fluorobenzene as a starting material compound is reacted with 1 mole of 4-fluorobenzoic acid chloride as a Friedel-Crafts reagent to produce as targeted compound (4,4'-difluoro)-benzophenone;

(vii) 1 mole of chlorobenzene as a starting material compound is reacted with 1 mole of 4-chloro-1-(chloromethyl)-benzene as a Friedel-Crafts reagent to produce as targeted compound (4,4'-dichloro)-phenylmethane;

(viii) 1 mole of chlorobenzene as a starting material compound is reacted with 1 mole of 4-fluoro-1-(chloromethyl)-benzene as a Friedel-Crafts reagent to produce as targeted compound (4-fluoro,4'-chloro)-phenylmethane;

(ix) 1 mole of fluorobenzene as a starting material compound is reacted with 1 mole of 4-chloro-1-(chloromethyl)-benzene as a Friedel-Crafts reagent to produce as targeted compound (4-fluoro,4'-chloro)-phenylmethane;

(x) 1 mole of fluorobenzene as a starting material compound is reacted with 1 mole of 4-fluoro-1-(chloromethyl)-benzene as a Friedel-Crafts reagent to produce as targeted compound (4,4'-difluoro)-phenylmethane;

(xi) 1 mole of chlorobenzene as a starting material compound is reacted with 1 mole of benzene-1,4-dicarbonyl dichloride as a Friedel-Crafts reagent to produce as targeted compound bis-1,4-[(4,4'-dichlorophenyl)-carbonyl]-phenylen;

(xii) 1 mole of fluorobenzene as a starting material compound is reacted with 1 mole of benzene-1,4-dicarbonyl dichloride as a Friedel-Crafts reagent to produce as targeted compound 1 bis-1,4-[(4,4'-difluorophenyl)-carbonyl]-phenylen.

In still another embodiment, the invention pertains to a process of preparing a compound according to the invention, wherein an aromatic ring of a starting material compound is reacted with a Friedel-Crafts reagent in the presence of an antimony pentahalide catalyst (SbHal$_5$), preferably in the presence of an activated antimony pentahalide catalyst (SbHal$_5$), optionally activated by hydrogen fluoride (HF), A) characterized in that the targeted compound is (4,4'-difluoro)-benzophenone, and further characterized in that
  (i) in a first step, 2 mole of chlorobenzene as a starting material compound is reacted with 1 mole of tetrachloromethane as a Friedel-Crafts reagent, in the presence of an antimony pentahalide catalyst (SbHal$_5$) activated by hydrogen fluoride (HF) present in low concentration, to produce as in situ as intermediate compound (4,4'-dichlorodiphenyl)-dichloromethane, and
  in a second step, the intermediate compound (4,4'-dichlorodiphenyl)-dichloromethane is reacted in the presence of an antimony pentahalide catalyst (SbHal$_5$) with hydrogen fluoride (HF) present in excess concentration, to produce as targeted compound (4,4'-difluoro)-benzophenone,
  or
  (ii) in a first step, 1 mole of chlorobenzene as a starting material compound is reacted with 1 mole of 4-chlorobenzoic acid chloride as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-benzophenone, and
  in a second step, the intermediate compound 4,4'-dichloro)-benzophenone is reacted in the presence of an antimony pentahalide catalyst (SbHal$_5$) with hydrogen fluoride (HF) present in excess concentration, to produce as targeted compound (4,4'-difluoro)-benzophenone,
  or
  (iii) in a first step, 1 mole of chlorobenzene as a starting material compound is reacted with 1 mole of (4-chlorophenyl) boronic acid as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-benzophenone, and
  in a second step, the intermediate compound 4,4'-dichloro)-benzophenone is reacted in the presence of an antimony pentahalide catalyst (SbHal$_5$) with hydrogen fluoride (HF) present in excess concentration, to produce as targeted compound (4,4'-difluoro)-benzophenone,
  or
B) characterized in that the targeted compound is (4,4'-difluoro)-phenylmethane, or optionally the targeted compound is (4,4'-difluoro)-benzophenone derived from the said (4,4'-difluoro)-phenylmethane,
and further characterized in that
  (iv) in a first step 1 mole of chlorobenzene as a starting material compound is reacted with 1 mole of 4-chloro-1-(chloromethyl)-benzene as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-phenylmethane, and
  in a second step, the intermediate compound (4,4'-dichloro)-phenylmethane is reacted in the presence of an antimony pentahalide catalyst (SbHal$_5$) with hydrogen fluoride (HF) present in excess concentration, to produce as targeted compound (4,4'-difluoro)-phenylmethane, optionally,
  wherein the (4,4'-difluoro)-phenylmethane obtained in the second step is further reacted to yield as the targeted compound is (4,4'-difluoro)-benzophenone;
  (v) in a first step chlorobenzene is reacted in the presence of an antimony pentahalide catalyst (SbHal$_5$) with hydrogen fluoride (HF) present in excess concentration, to produce as in situ as intermediate compound fluorobenzene, and
  in a second step, the 1 mole of the intermediate compound fluorobenzene is reacted with 1 mole of tetrachloromethane as a Friedel-Crafts reagent, in the presence of an antimony pentahalide catalyst (SbHal$_5$) activated by hydrogen fluoride (HF) present in low concentration, to produce as targeted compound (4,4'-difluoro)-phenylmethane, optionally,
  wherein the (4,4'-difluoro)-phenylmethane obtained in the second step is further reacted to yield as the targeted compound is (4,4'-difluoro)-benzophenone;
C) characterized in that the targeted compound is bis-1,4-[(4,4'-difluorophenyl)-carbonyl]-phenylene,
and further characterized in that
  (vi) 1 mole of chlorobenzene as a starting material compound is reacted with 1 mole of benzene-1,4-dicarbonyl dichloride as a Friedel-Crafts reagent, in the presence of an antimony pentahalide catalyst (SbHal$_5$) activated by hydrogen fluoride (HF) present in low concentration, to produce as in situ as intermediate compound bis-1,4-[(4,4'-dichlorophenyl)-carbonyl]-phenylene, and
  in a second step, the intermediate compound bis-1,4-[(4,4'-dichlorophenyl)-carbonyl]-phenylene is reacted in the presence of an antimony pentahalide catalyst (SbHal$_5$) with hydrogen fluoride (HF) present in excess concentration, to produce as targeted compound bis-1,4-[(4,4'-difluorophenyl)-carbonyl]-phenylenee.

The Concentration of HF:

The meaning of the term "low", in the context of the Friedel-Crafts reaction, is a concentration of at least an amount of traces of HF, e.g., traces of HF in the range of from about 0.1 ppm to about 100 ppm. Such amounts in ppm-traces of HF can be employed if, for example, the starting material, a reaction partner, or the desired product is used as the solvent. Alternatively, an inert solvent can also be used, e.g., hexafluorobenzene or perfluorodecaline can be used as solvents. In some embodiments the HF-concentration may even be as low as about zero, or even zero (HF is absent).

For the fluorination at the benzene nucleus one needs then of course "excess" HF so that nucleophilic fluorinating $H_2F^+SbF_6^-$-species forms.

Regarding the excess of HF, there is no method of analysis required to determine the amount of $H_2F^+SbF_6^-$-species, but it can be estimated that starting at about a 2-times molar excess of HF as compared to the molar amount of Sb can be regarded as the lower value required as the lower limit already forms sufficient content of the $H_2F^+SbF_6^-$-species in the reaction mixture. The upper limit is not critical, and can be up to an infinite surplus, however for practical reason, of course, the upper limit of HF is chosen such that it is adapted to the molar amount of fluorine needed in the fluorination reaction and for having a not too diluted reaction mixture. Accordingly, in an embodiment of the fluorination reaction, the upper limit of HF can be up to about 40-times molar excess of HF as compared to the molar amount of Sb. In another embodiment of the fluorination reaction, the upper limit of HF can be up to about 30-times molar excess, preferably the upper limit of HF can be up to about 20-times molar excess, more preferably the upper limit of HF can be up to about 10-times molar excess, of HF, each as compared to the molar amount of Sb. It is to be noted, as in a particular case it may be, that an HF excess can also have a very positive effect on a better phase separation.

Thus, the excess HF-concentration in the fluorination reaction, as compared to the molar amount of Sb, is in the range of about 2-times excess of HF up to about 40-times molar excess of HF. In another embodiment of the fluorination reaction, the excess HF-concentration in the fluorination reaction, each as compared to the molar amount of Sb, is in the range of about 2-times excess of HF up to a about 30-times molar excess of HF, preferably is in the range of about 2-times excess of HF up to about 20-times molar excess, more preferably is in the range of about 2-times excess of HF up to about 10-times molar excess.

In a further embodiment, the invention pertains to a process of preparing a compound by Friedel-Crafts reaction according to any one of the processes of the invention as defined above, characterized in that
(a) the reaction is performed in the presence of an antimony pentahalide catalyst (SbHal$_5$), preferably in the presence of an activated antimony pentahalide catalyst (SbHal$_5$), optionally activated by hydrogen fluoride (HF), and in that the process is a continuous process;
or
(b) in case the process comprises two or more steps, comprising
(b1) as one of the steps a Friedel-Crafts reaction, wherein a starting material compound is reacted with a Friedel-Crafts reagent, in the presence of an antimony pentahalide catalyst (SbHal$_5$), optionally activated by hydrogen fluoride (HF) present in low concentration, and
(b2) one of the steps a fluorination reaction, wherein a compound is reacted in the presence of an antimony pentahalide catalyst (SbHal$_5$) with hydrogen fluoride (HF) present in excess concentration,
wherein at least one of the said steps (b1) and (b2) is a continuous process, preferably wherein of the said steps at least (b2) the step of a fluorination reaction is a continuous process,
more preferably wherein of the said steps (b1) of Friedel-Crafts reaction, and (b2) of fluorination reaction both are a continuous process.

For example, in a process of preparing a compound as defined above, according to the invention, at least one of the said continuous processes of the said steps (b1) and (b2),
preferably wherein of the said steps at least (b2) the step of a fluorination reaction is a continuous process,
more preferably wherein of the said steps (b1) of Friedel-Crafts reaction, and (b2) of fluorination reaction both are a continuous process,
wherein the continuous process is performed in at least one continuous flow reactor with upper lateral dimensions of about ≤5 mm, or of about ≤4 mm, preferably in at least one microreactor;
most preferably wherein of the said steps at least (b2) the step of a fluorination reaction is a continuous process in at least one microreactor under one or more of the following conditions:
flow rate: of from about 10 ml/h up to about 400 l/h;
temperature: of from about 30° C. up to about 150° C.;
pressure: of from about 4 bar up to about 50 bar;
residence time: of from about 1 second, preferably from about 1 minute, up to about 60 minutes.

In still a further embodiment, the invention pertains to a process of preparing a compound as defined above, according to the invention, wherein at least one of the said continuous flow reactors, preferably at least one of the microreactors, independently is a SiC-continuous flow reactor, preferably independently is a SiC-microreactor.

In yet a further embodiment, the invention pertains to a process of preparing a compound, as defined above, according to the invention, wherein in the fluorination reaction the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+SbF_6^-$.

For example, in a process of preparing a compound as defined above, according to the invention, in the fluorination reaction the halogenation catalyst is antimony pentachloride and/or antimony pentafluoride, preferably wherein the catalyst is antimony pentafluoride (SbF$_5$) and is prepared in an autoclave by reaction of SbCl$_5$ with HF, more preferably consisting of SbF$_5$ in HF which forms the active species $H_2F^+SbF_6^-$, prior to a reaction step in the process according to any one of the embodiments of the invention.

In yet another embodiment, the invention pertains to a process of preparing a compound, as defined above, according to the invention, wherein the process comprises in step (b3) purifying and/or isolating the targeted compound obtained in a process of preparing a compound as defined in any one of the preceding embodiments of the invention, to yield the said purified and/or isolated compound.

For example, in a process, as defined above, according to the invention, in step (b3) the purifying and/or isolating of the targeted compound comprises or consists of a phase separation method, preferably wherein in step (b3) the purifying and/or isolating of the targeted compound does not comprise a distillation to yield purified and/or isolated targeted compound.

All reactions described can be carried out in the batch reactor or continuously in plug-flow or microreactors, as further explained in the scheme of FIG. 1, using the microreactor example. Since SbV can be reduced partially to SbIII, optionally halogen in the form of chlorine or fluorine can be fed to any HF/catalyst recycle stream downstream of the phase separator (see WO03/053580).

Moreover, since the mixture of highly fluorinated antimony (Sb) catalyst with excess HF is very corrosive, according to the invention, these reactions most preferably are carried out in SiC reactors or in HDPDFE coated reactors, or in reactors that lined accordingly with SiC or HDPDFE. Also some Al coatings have positive resistance.

If the end product is a solid, the purification is preferably carried out by recrystallization. If the product is a liquid or low-melting solid, it is purified by distillation, optionally by so-called solid distillation with heated condenser.

Further Details on the Reactors:

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to amicroreactor or several microreactors in series for increasing residence time. Continuously operated series of STRs is another option, but less preferred than using a microreactor.

It is to be noted that between two of any of the microreactors, a cyclone, as is already mentioned herein, may advantageously be interposed, e.g., in order to, at least partially, remove HCl formed in the reaction.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behavior of chemical reactors of such design, so that key reactor variables, such as the dimensions of the reactor, can be estimated.

Fluid going through a PFR may be modeled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm or even smaller, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, then the said solid raw materials are dissolved in an inert solvent. A suitable solvent is e.g. acetonitrile, or fully or partially fluorinated alkanes like pentafluorobutane (365mfc), linear or cyclic partially or fully fluorinated ethers like $CF_3$—$CH_2$—$OCHF_2$ (E245) or compounds like octafluorotetrahydrofuran and derivatives. Often, if available or after a first synthesis, the product as such can also serve as inert solvent.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is conFig.d with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrixmodules are fabricated from 3M™ SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakage might occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

Further Details of the Fluorination Process of the Invention:

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$.

In one embodiment, the invention relates to a fluorination process for the manufacture of the fluorinated products according to the invention, wherein at least one of the said continuous flow reactors, preferably at least one of the microreactors, independently is a SiC-continuous flow reactor, preferably independently is an SiC-microreactor.

In another embodiment, the invention relates to a fluorination process according to any one of the embodiments described herein, related to the manufacture of the fluorinated products according to the invention, wherein the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+SbF_6^-$.

In yet another embodiment, the invention relates to a fluorination process according to any one of the embodiments described herein, related to the manufacture of the fluorinated products according to the invention, wherein the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in high molar excess of HF which forms the active species $H_2F^+SbF_6^-$, prior to fluorination reaction step in the process according to any one of embodiments described herein, related to the manufacture of the fluorinated products according to the invention.

In a further embodiment, the invention relates to a fluorination process according to any one of the preceding embodiments described herein, related to the manufacture of the fluorinated products according to the invention, wherein the process comprises purifying and/or isolating the fluorinated product obtained to yield purified and/or isolated fluorinated products according to the invention.

In yet a further embodiment, the invention relates to a fluorination process according to any one of the preceding embodiments described herein, related to the manufacture of the fluorinated products according to the invention, wherein the purifying and/or isolating of the fluorinated product comprises or consists of a phase separation method.

In still a further embodiment, the invention relates to a fluorination process according to any one of the preceding embodiments described herein, related to the manufacture of the fluorinated products according to the invention, wherein the purifying and/or isolating does not comprise a distillation to yield purified and/or isolated fluorinated products according to the invention.

Further Details of the Reactors Used in the Invention:

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm, or of about ≤4 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤5 mm, or of about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤5 mm, or of about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is conFig.d with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic or high grade stainless steel (Inox or Hastelloy) continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld.

In order to meet both the mechanical and chemical demands placed on production scale flow reactors, Plantrixmodules are fabricated from 3M™ SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows; possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300× 250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multi-purpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0.35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the targeted compounds described herein in the context of the invention. If more than one microreactor, preferably more than one SiC-microreactors, are used in the production, preferably in the industrial production, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)<70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The following examples are intended to further illustrate the invention without limiting its scope.

EXAMPLES

Example 1

The synthesis flow in microreactors for 4,4'-difluorobenzophenone is shown in FIG. 1, and the reaction scheme and the conditions are given below.

4-Chlorobenzoylchloride is pre-mixed with the HF+catalyst mixture, preferably in a mixing system (e.g., a split and recombine system) to form at least partially chlorobenzoylfluoride and the corresponding SbHal$_6$-complex which meets the chlorobenzene before the mixture enters microreactor 1 (material of construction is SiC).

The reaction is performed as a two-step procedure, comprising a fluorination step and a Friedel-Crafts reaction.

Chemistry in step 1 (Microreactor 1), Friedel-Crafts Acylation:

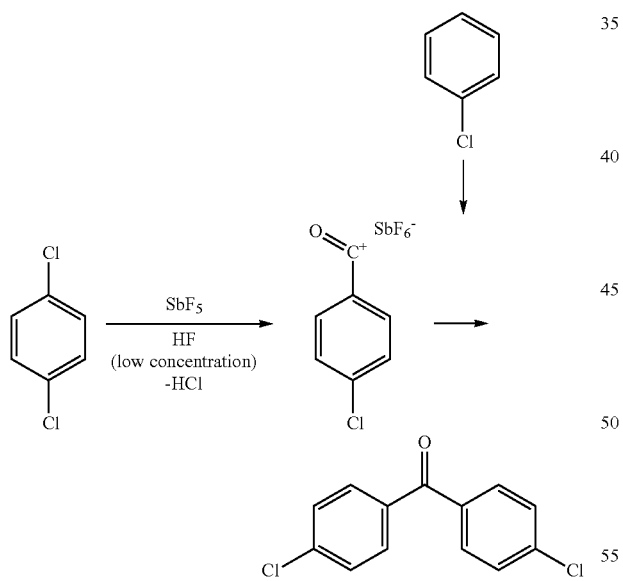

If a settler of sufficient size is used, the HF-catalyst mixture will separate from organic material which mainly is the 4,4'-dichlorobenzophenone. In the next step the HF/catalyst mixture needs to be converted into a nucleophilic fluorinating agent by adding an excess of HF vs. the Sb molar ratio which should be greater than 10 (HF:Sb=>10:1) before it enters microreactor 2. The reaction is also possible without a settler after microreactor 1 and without phase separation, but process control in industrial scale might be easier with that concept and a settler after microreactor 1.

So the either just to the organic phase (if a settler is used) or to the mixture leaving microreactor 1 is added an excess of water free HF to get chemically this nucleophilic fluorinating agent to convert 4,4'-dichlorobenzophenone into 4,4'-difluorobenzophenone.

Chemistry in step 2 (Microreactor 2), Fluorination Step:

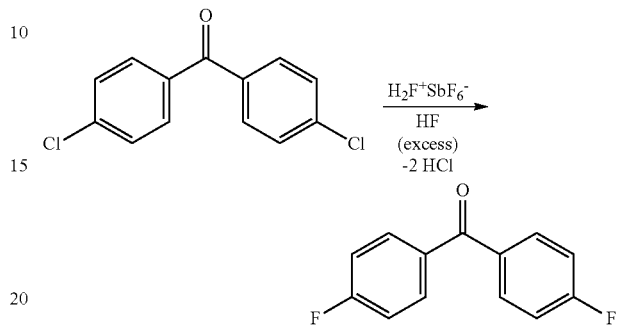

After microreactor 2, there is another settler with sufficient residence time allowing phase separation of the excess HF/Sb-mixture and 4,4'-difluorobenzophenone. Remaining HF can be removed out of the product by a $N_2$— or other inert gas stream or vacuum followed by re-crystallisation or so called solid phase distillation apparatus in vacuum with a heated cooler. The melting point after re-crystallisation was 109° C.

Example 2

Figure 2:
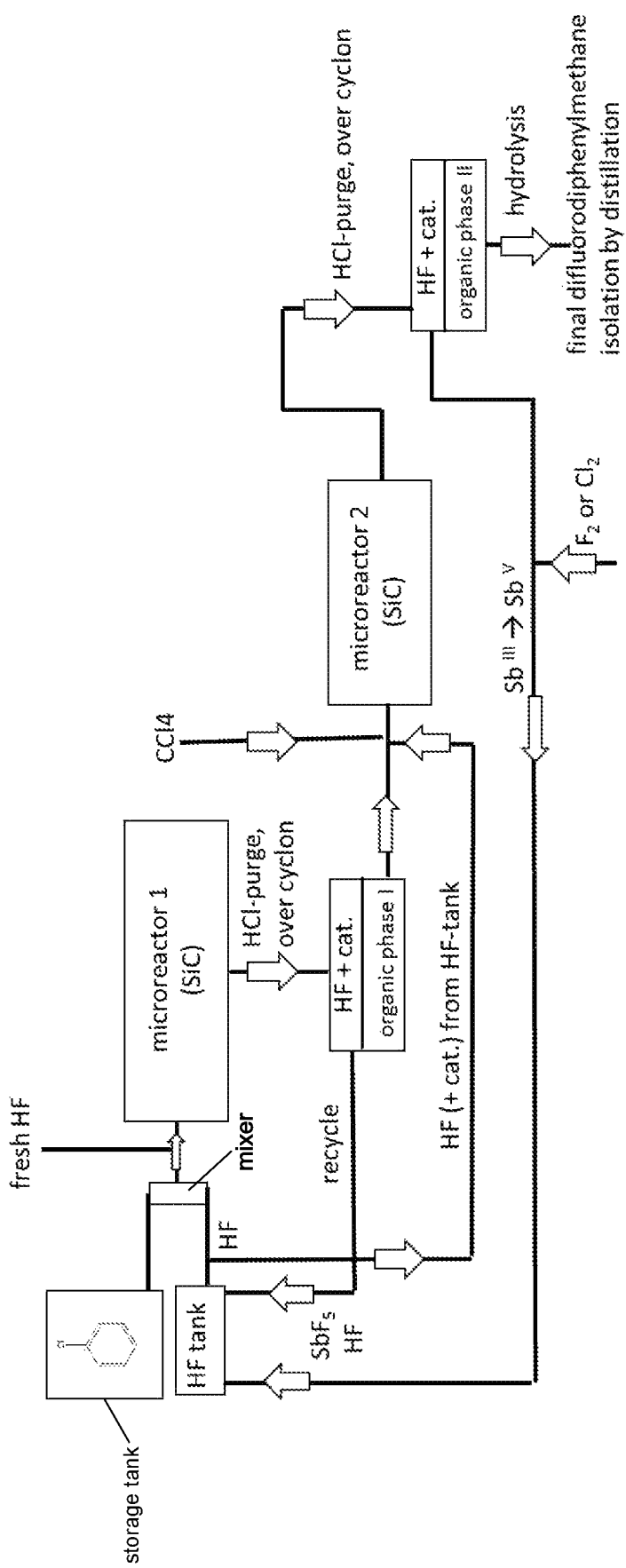
In FIG. 2, shows an exemplary embodiment of a process scheme for the continuous manufacture of 4,4'-difluorophenylmethane out of $CCl_4$ and chlorobenzene, for example, by synthesis in microreactor.

The CCl$_4$-route according to the invention is shown in FIG. 2, and the reaction scheme is given below. The reaction conditions are as given in Example 1.

If the CCl$_4$-route is used, it is advantageous first to prepare fluorobenzene and to do in a 2nd step the Friedel-Crafts with CCl$_4$, like illustrated in the scheme below:

Chemistry in Step 1 (Microreactor 1), Fluorination Step:

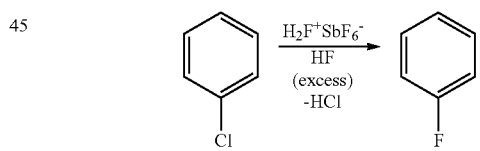

Chemistry in Step 2 (Microreactor 2), Friedel-Crafts Acylation:

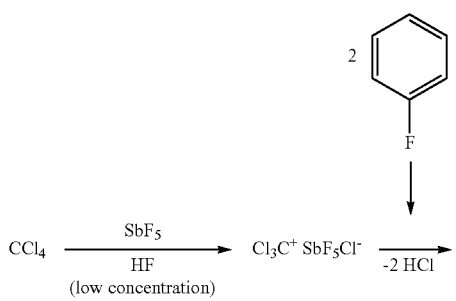

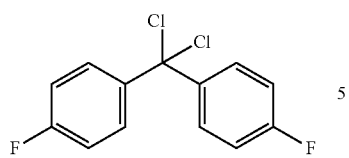

Step 3, Hydrolysis:

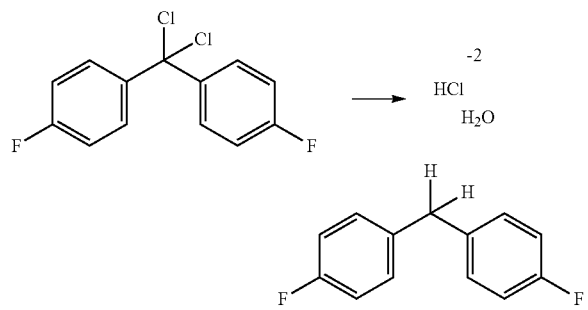

Example 3

Figure 3:
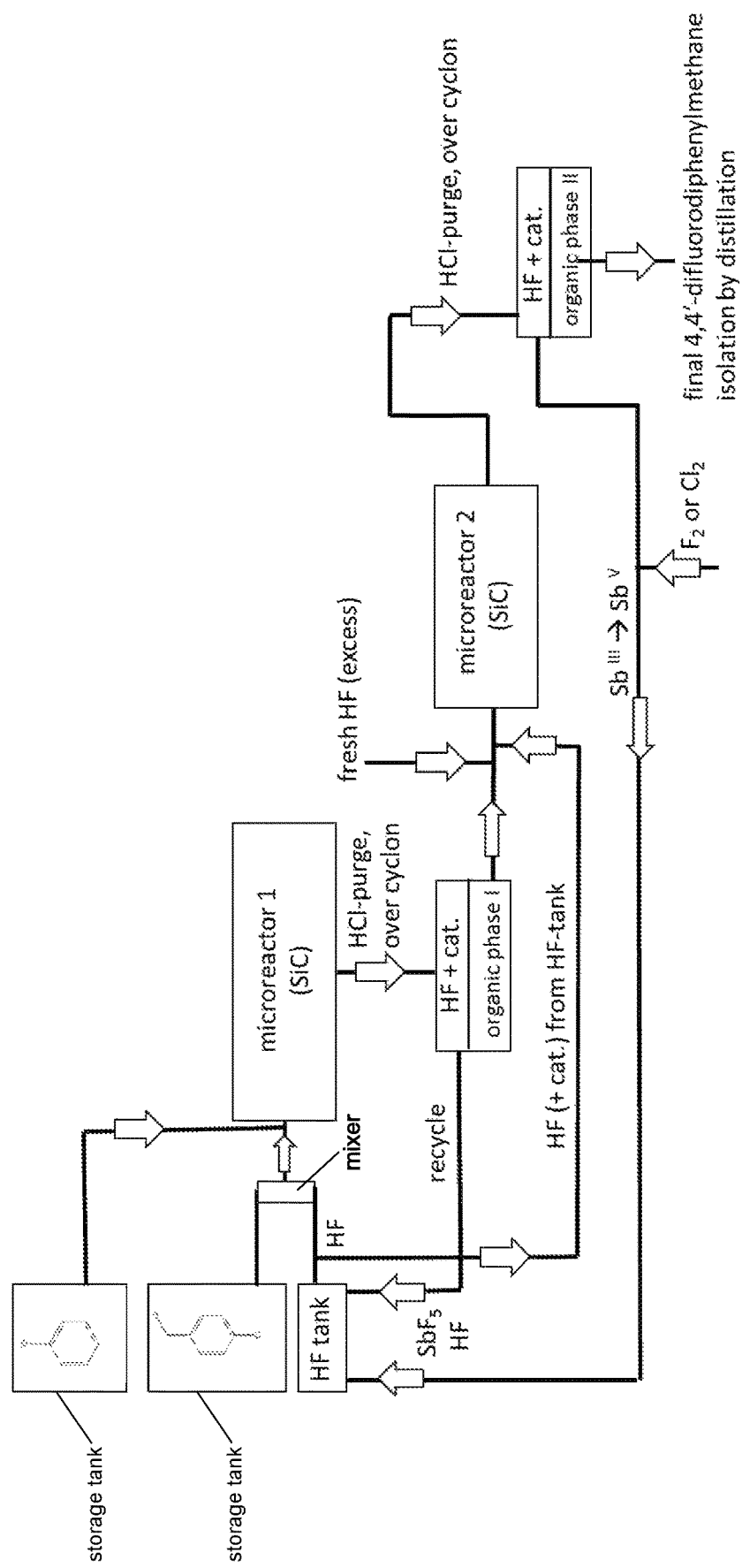
In FIG. 3, shows an exemplary embodiment of a process scheme for the continuous manufacture of 4,4'-difluorophenylmethane out of 4-chlorbenzylchloride and chlorobenzene, for example, by synthesis in microreactor.

The 4-chlorobenzylchlorid route according to the invention is shown in FIG. 3, and the reaction scheme is given below. The reaction conditions are as given in Example 1.

Chemistry in Step 1 (Microreactor 1), Friedel-Crafts Acylation:

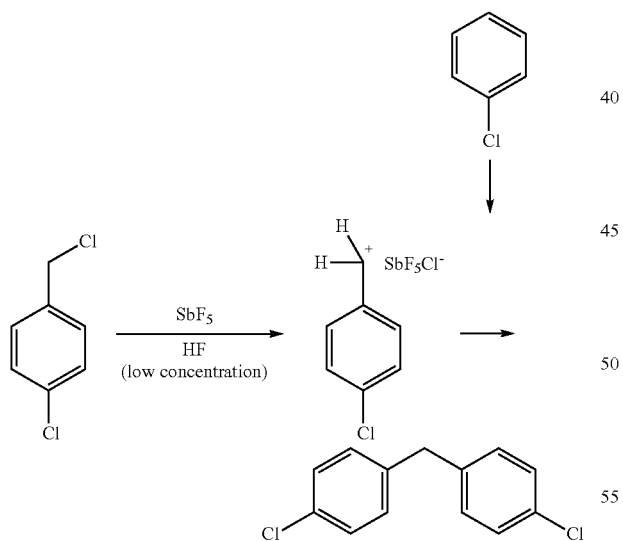

Chemistry in Step 2 (Microreactor 2), Fluorination Step:

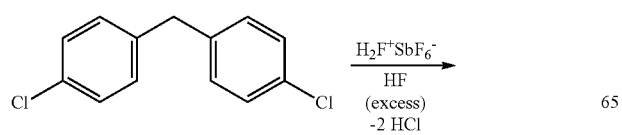

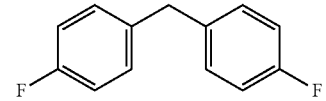

What is claimed is:

1. A process of preparing a compound comprising one or more aromatic rings by Friedel-Crafts reaction, characterized in that an aromatic ring of a starting material compound is reacted with a Friedel-Crafts reagent in the presence of an activated antimony pentahalide catalyst (SbHal$_5$), activated by hydrogen fluoride (HF); wherein A) characterized in that the targeted compound is (4,4'-difluoro)-benzophenone, and further characterized in that (i) in a first step, 2 mole of chlorobenzene as a starting material compound is reacted with 1 mole of tetrachloromethane as a Friedel-Crafts reagent, in the presence of an antimony pentahalide catalyst (SbHal$_5$) activated by hydrogen fluoride (HF) present in low concentration, to produce as in situ as intermediate compound (4,4'-dichlorodiphenyl)-dichloromethane, and in a second step, the intermediate compound (4,4'-dichlorodiphenyl)-dichloromethane is reacted in the presence of an antimony pentahalide catalyst (SbHal$_5$) with hydrogen fluoride (HF) present in excess concentration, to produce as targeted compound (4,4'-difluoro)-benzophenone, or (ii) in a first step, 1 mole of chlorobenzene as a starting material compound is reacted with 1 mole of 4-chlorobenzoic acid chloride as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-benzophenone, and in a second step, the intermediate compound 4,4'-dichloro)-benzophenone is reacted in the presence of an antimony pentahalide catalyst (SbHal$_5$) with hydrogen fluoride (HF) present in excess concentration, to produce as targeted compound (4,4'-difluoro)-benzophenone, or (iii) in a first step, 1 mole of chlorobenzene as a starting material compound is reacted with 1 mole of (4-chlorophenyl) boronic acid as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-benzophenone, and in a second step, the intermediate compound 4,4'-dichloro)-benzophenone is reacted in the presence of an antimony pentahalide catalyst (SbHal$_5$) with hydrogen fluoride (HF) present in excess concentration, to produce as targeted compound (4,4'-difluoro)-benzophenone, or B) characterized in that the targeted compound is (4,4'-difluoro)-phenylmethane, or the targeted compound is (4,4'-difluoro)-benzophenone derived from the said (4,4'-difluoro)-phenylmethane, and further characterized in that
- (iv) in a first step 1 mole of chlorobenzene as a starting material compound is reacted with 1 mole of 4-chloro-1-(chloromethyl)-benzene as a Friedel-Crafts reagent, in the presence of an antimony pentahalide catalyst (SbHal$_5$) activated by hydrogen fluoride (HF) present in low concentration, to produce as in situ as intermediate compound (4,4'-dichloro)-phenylmethane, and
  in a second step, the intermediate compound (4,4'-dichloro)-phenylmethane is reacted in the presence of an antimony pentahalide catalyst (SbHal$_5$) with hydrogen fluoride (HF) present in excess concentration, to produce as targeted compound (4,4'-difluoro)-phenylmethane,
  wherein the (4,4'-difluoro)-phenylmethane obtained in the second step is further reacted to yield as the targeted compound is (4,4'-difluoro)-benzophenone,
- (v) in a first step chlorobenzene is reacted in the presence of an antimony pentahalide catalyst (SbHal$_5$) with hydrogen fluoride (HF) present in excess concentration, to produce as in situ as intermediate compound fluorobenzene, and
  in a second step, the 1 mole of the intermediate compound fluorobenzene is reacted with 1 mole of tetrachloromethane as a Friedel-Crafts reagent, in the presence of an antimony pentahalide catalyst (SbHal$_5$) activated by hydrogen fluoride (HF) present in low concentration, to produce as targeted compound (4,4'-difluoro)-phenylmethane,
  wherein the (4,4'-difluoro)-phenylmethane obtained in the second step is further reacted to yield as the targeted compound is (4,4'-difluoro)-benzophenone,
- C) characterized in that the targeted compound is bis-1,4-[(4,4'-difluorophenyl)-carbonyl]-phenylene, and further characterized in that
- (vi) 1 mole of chlorobenzene as a starting material compound is reacted with 1 mole of benzene-1,4-dicarbonyl dichloride as a Friedel-Crafts reagent, in the presence of an antimony pentahalide catalyst (SbHal$_5$) activated by hydrogen fluoride (HF) present in low concentration, to produce as in situ as intermediate compound bis-1,4-[(4,4'-dichlorophenyl)-carbonyl]-phenylene, and
  in a second step, the intermediate compound bis-1,4-[(4,4'-dichlorophenyl)-carbonyl]-phenylene is reacted in the presence of an antimony pentahalide catalyst (SbHal$_5$) with hydrogen fluoride (HF) present in excess concentration, to produce as targeted compound bis-1,4-[(4,4'-difluorophenyl)-carbonyl]-phenylene.

2. The process of preparing a compound according to claim 1, wherein the catalyst is a fluorination catalyst wherein the fluorination catalyst is selected from the group consisting of Sb fluorination catalysts providing the active species $H_2F^+SbF_6^-$.

3. The process of preparing the compound according to claim 2, wherein the catalyst is antimony pentafluoride (SbF$_5$) activated by HF which forms the active species $H_2F^+SbF_6^-$.

4. The process of preparing a compound according to claim 1, wherein the process comprises a step (b3) purifying and/or isolating the targeted compound obtained in a process of preparing a compound as defined in claim 1, to yield the said purified and/or isolated compound.

5. The process according to claim 4, wherein the step (b3) the purifying and/or isolating of the targeted compound comprises or consists of a phase separation method.

6. The process according to claim 5, wherein the step (b3) the purifying and/or isolating of the targeted compound does not comprise a distillation to yield purified and/or isolated targeted compound.

* * * * *